United States Patent
Park et al.

(10) Patent No.: US 11,222,725 B2
(45) Date of Patent: Jan. 11, 2022

(54) DEVICE FOR ACQURING PERSONAL HEALTH INFORMATION AND METHOD THEREFOR

(71) Applicant: ARAM HUVIS CO., LTD., Gyeonggi-do (KR)

(72) Inventors: Dong Soon Park, Yongin-si (KR); Jeong Il Jeong, Seoul (KR)

(73) Assignee: ARAM HUVIS CO., LTD., Seongnam-si (KR)

( * ) Notice: Subject to any disclaimer, the term of this patent is extended or adjusted under 35 U.S.C. 154(b) by 847 days.

(21) Appl. No.: 15/747,249

(22) PCT Filed: Jul. 22, 2016

(86) PCT No.: PCT/KR2016/008010
§ 371 (c)(1),
(2) Date: Jan. 24, 2018

(87) PCT Pub. No.: WO2017/022986
PCT Pub. Date: Feb. 9, 2017

(65) Prior Publication Data
US 2018/0218787 A1   Aug. 2, 2018

(30) Foreign Application Priority Data
Aug. 5, 2015 (KR) ........................ 10-2015-0110642

(51) Int. Cl.
*G16H 40/63* (2018.01)
*A61B 5/01* (2006.01)
(Continued)

(52) U.S. Cl.
CPC ......... *G16H 40/63* (2018.01); *A61B 1/00018* (2013.01); *A61B 1/00105* (2013.01);
(Continued)

(58) Field of Classification Search
CPC ........ G16H 40/63; G16H 50/20; G16H 30/40; A61B 1/00018; A61B 1/00105;
(Continued)

(56) References Cited

FOREIGN PATENT DOCUMENTS

JP   2000-175871 A    6/2000
KR   20-0291667 Y1   10/2002
(Continued)

*Primary Examiner* — Aaron F Roane
(74) *Attorney, Agent, or Firm* — John K. Park; Park Law Firm

(57) ABSTRACT

The invention relates to a device for acquiring personal health information and a method therefor, the device: easily and periodically acquiring, anytime and anywhere or without regard to place and time, information on ambient temperature/humidity and health information of an individual, such as the state of skin (including hair), a nose, ears, and a mouth associated with an ENT clinic, the teeth associated with a dental clinic, skin moisture, and body temperature, through image information having multiple functions and a multifunctional health care sensor; enabling the acquired health information to be accumulated over in a personal terminal or computer by analyzing, storing, and making the same into data, and continuously managing the periodically accumulated personal health information such that the personal health information can be used as critical information by which a disease cause and the like can be fundamentally understood during an incidence of disease in the future.

3 Claims, 5 Drawing Sheets

(51) Int. Cl.
- *A61B 1/05* (2006.01)
- *A61B 1/00* (2006.01)
- *A61B 1/06* (2006.01)
- *G16H 30/40* (2018.01)
- *G16H 50/20* (2018.01)
- *A61B 1/227* (2006.01)
- *A61B 1/233* (2006.01)
- *A61B 1/24* (2006.01)
- *A61B 5/00* (2006.01)
- *A61B 90/30* (2016.01)

(52) U.S. Cl.
CPC ............ *A61B 1/00108* (2013.01); *A61B 1/05* (2013.01); *A61B 1/0676* (2013.01); *A61B 1/0684* (2013.01); *A61B 1/227* (2013.01); *A61B 1/233* (2013.01); *A61B 1/24* (2013.01); *A61B 5/0008* (2013.01); *A61B 5/0013* (2013.01); *A61B 5/0077* (2013.01); *A61B 5/01* (2013.01); *A61B 5/443* (2013.01); *A61B 5/4547* (2013.01); *G16H 30/40* (2018.01); *G16H 50/20* (2018.01); *A61B 2090/309* (2016.02); *A61B 2560/0252* (2013.01); *A61B 2562/029* (2013.01); *A61B 2562/227* (2013.01); *A61B 2576/00* (2013.01)

(58) Field of Classification Search
CPC ..... A61B 1/00108; A61B 1/05; A61B 1/0676; A61B 1/0684; A61B 1/227; A61B 1/233; A61B 1/24; A61B 5/0008; A61B 5/0013; A61B 5/0077; A61B 5/01; A61B 5/443; A61B 5/4547; A61B 2090/309; A61B 2560/0252; A61B 2562/029; A61B 2562/227; A61B 2576/00
USPC ........................................................ 600/301
See application file for complete search history.

(56) References Cited

FOREIGN PATENT DOCUMENTS

| | | |
|---|---|---|
| KR | 10-2010-0030919 A | 3/2010 |
| KR | 10-1274303 B1 | 6/2013 |
| WO | 2012127870 | 9/2012 |

DEVICE FOR ACQURING PERSONAL HEALTH INFORMATION AND METHOD THEREFOR

TECHNICAL FIELD

The present invention relates to a device for acquiring personal health information and a method therefor and, more particularly, to a device and a method for easily and periodically acquiring, without regard to place and time, personal health information and enabling the acquired health information to be accumulated over a long time by analyzing, storing, and making the same into data, and continuously managing the periodically accumulated personal health information such that the personal health information can be used as critical information by which a disease cause can be fundamentally understood during an incidence of a disease in the future.

BACKGROUND ART

In general, in order to diagnose whether the skin (including the hair), the nose, the ears, the mouth, the teeth, skin moisture, and body temperature of a human body are in a normal state or in an early stage of disease, a person needs to visit a hospital, wherein the person should be examined using expensive medical equipment and should be consulted by a specialist.

Therefore, general individual consumers have to set aside time to visit a hospital and must pay for expensive medical care, resulting in a difficulty in receiving periodic and continuous examinations for these reasons.

If a disease develops in the human body at a certain point of time, the disease can be more accurately diagnosed and prescribed if information, such as life patterns, eating habits, and the surrounding environment of the person, has been continuously and periodically been accumulated by analyzing, storing, and making the same into data over a long period of time.

In particular, when information on the skin such as state of sebum, pores, melanin, acne, wrinkles, sensitivity, and moisture is continuously and periodically acquired from the skin of the human body over a long period of time to enable the acquired information to be accumulated by analyzing, storing, and making the same into data, a correct cosmetic prescription can be made when a skin disease occurs or when selecting a cosmetic.

However, it is impossible that an individual acquires personal health information periodically and continuously over a long period of time and enables the acquired information to be accumulated by analyzing, storing, and making the same into data, in daily lives, anytime and anywhere or without regard to place and time.

In addition, expensive equipment must be provided in order to acquire health information of an individual.

DISCLOSURE

Technical Problem

The present invention has been made in view of the above problems, and it is an object of the present invention to obtain a device for acquiring personal health information and a method therefor, which is capable of easily and periodically acquiring, anytime and anywhere or without regard to place and time, information on ambient temperature/humidity and personal health information such as a state of the skin (including the hair), the nose, the ears, and the mouth associated with an ENT clinic, the teeth associated with a dental clinic, skin moisture, and body temperature through image information having multiple functions and a multifunctional health care sensor; enabling the acquired health information to be accumulated over a long time in a personal terminal (Android) or a personal computer (PC) by analyzing, storing, and making the same into data; and continuously managing the periodically accumulated personal health information of a user such that the personal health information can be used as critical information by which a disease cause and the like can be fundamentally understood during an incidence of a disease in the future.

Technical Solution

In order to accomplish the above object, the present invention provides a device for acquiring personal health information that includes, as an image information acquiring unit for acquiring image information on any one of a skin image used to diagnose skin; an ear, a nose, and a mouth image used to diagnose an ear, a nose, and a throat; and a teeth image used to diagnose teeth, an LED light for emitting light to a subject to cause the light to be projected thereon, an LED driver for driving the LED light, a general purpose input/output (GPIO) expander for controlling the LED driver to turn on the LED light, a lens for passing image information projected and reflected by the LED light, and a CAM sensor (C-MOS sensor) for receiving the image information that has passed through the lens and converting the image information into a YUV video signal to be transmitted to a USB back end 5, the device includes:

a moisture sensor for acquiring moisture of skin with a built-in microcomputer to cause the acquired information to be transmitted to the USB back end via I2C communication a human body temperature sensor for acquiring body temperature of a human body with a built-in microcomputer to cause the acquired information to be transmitted to the USB back end via I2C communication, a temperature/humidity sensor for acquiring an ambient temperature and humidity of a person who undergoes an examination with a built-in microcomputer (not shown) to cause the acquired information to be transmitted to the USB back end via I2C communication, the USB back end for causing the image information received as the YUV signal from the CAM sensor in the image information acquiring unit and the health care information received from the moisture sensor, the human body temperature sensor, and the temperature/humidity sensor via I2C communication to be converted into a USB standard signal, in which the image information and the health care information transmitted to the USB back end are transmitted as a USB standard signal to a personal terminal (Android) or a personal computer (PC)(Windows, Mac OS) via a USB port, and an electrically erasable programmable read-only memory EEPROM for communicating with the USB back end via I2C communication to allow the USB back end to make a correct and smooth interface between the CAM sensor, the moisture sensor, the human body temperature sensor, and the temperature/humidity sensor, and the personal terminal (Android) and the personal computer (Windows, Mac OS) for the image information and the health care information.

In order to accomplish the above object of the present invention, the present invention provides a method for acquiring personal health information as another embodiment, the method includes selecting a mode for acquiring desired information of skin image information as personal health information and skin moisture, body temperature, and ambient temperature and humidity of a person who undergoes an examination as health care information, acquiring the skin image information, when the skin image information is selected in the selecting the mode, by allowing an LED light to be emitted to skin desired to acquire health information to cause the light to be projected thereon, thereby causing a skin image reflected from the skin to be received by a CAM sensor through a lens, and the received image information to be converted into an image signal YUV signal and transmitted to a USB back end, storing the skin image information, by allowing the YUV signal to be converted into a USB standard signal in the USB back end, transmitted to a personal terminal (Android) or a personal computer (PC) via a USB port, and displayed as an image on a display in the personal terminal A or the personal computer B, thereby causing the acquired skin image information to be accumulated by analyzing, storing, and making the same into data, acquiring the health care information, when selecting a mode for acquiring desired information of skin moisture, body temperature, and ambient temperature and humidity of a person who undergoes an examination as health care information in the selecting the mode, by allowing information to be acquired using a moisture sensor, a human body temperature sensor, and an ambient temperature/humidity sensor having built-in microcomputer, thereby causing the acquired information to be analyzed from the moisture sensor, the human body temperature sensor, and the ambient temperature/humidity sensor and transmitted to the USB back end via I2C communication, and completing the method, by allowing the health care information transmitted to the USB back end to be transmitted to the personal terminal or the personal computer via the USB port and be displayed as an image on a display in the personal terminal (Android) or the personal computer (PC), thereby causing the acquired health care information to be accumulated by storing or making the same into data.

Advantageous Effects

According to the present invention, it is possible to easily and periodically acquire, anytime and anywhere or without regard to place and time, information on ambient temperature/humidity and health information of an individual, such as the skin (including the hair), the nose, the ears, and the mouth associated with an ear, nose, and throat (ENT) clinic, the teeth which are associated with a dental clinic, skin moisture, and body temperature through image information having multiple functions and a multifunctional health care sensor; enable the acquired health information to be accumulated over a long time in a personal terminal (Android) or a personal computer (PC) by analyzing, storing, and making the same into data and diagnosed and treated as necessary; and continuously manage the periodically accumulated personal health information of a user such that the personal health information can be used as critical information by which a disease cause and the like can be fundamentally understood during an incidence of a disease in the future.

In other words, by continuously accumulating personal health information, such as a state of the skin (including the hair), a state of the nose, the ears, and the mouth associated with an ENT clinic, a state of the teeth associated with a dental clinic, skin moisture, body temperature, and ambient temperature/humidity over a long period of time, a disease cause may be fundamentally understood during an incidence of a disease in the future; each user may analyze and diagnose himself/herself according to his/her own operating programs as necessary in order not to miss a time when he/she must be treated by a specialist; and in particular, information on the skin such as a state of sebum, pores, melanin, acne, wrinkles, sensitivity, and moisture is continuously and periodically acquired from the skin over a long period of time to enable the acquired information to be analyzed, stored, and made into data, whereby a correct cosmetic prescription and a management plan or treatment method can be prescribed, or information such as cosmetics suitable to the skin can be provided when a skin disease occurs or when selecting a cosmetic.

DESCRIPTION OF DRAWINGS

FIGS. 2a and 2b are views for illustrating a device for acquiring skin image information and health care information according to the present invention, in which FIG. 2a is an overall sectional view and FIG. 2b is an enlarged sectional view of a main part.

FIGS. 3a and 3b are views showing a device for acquiring image information on the nose, the ears, and the mouth and health care information according to the present invention, in which FIG. 3a is an overall sectional view and FIG. 3b is an enlarged sectional view of a main part.

FIGS. 4a and 4b are views showing a device for acquiring teeth image information and health care information of according to the present invention, in which FIG. 4a is an overall sectional view and FIG. 4b is an enlarged sectional view of the main part.

BEST MODE

Hereinafter, preferred embodiments of the present invention will be described in detail with reference to the accompanying drawings.

Figure 1A:
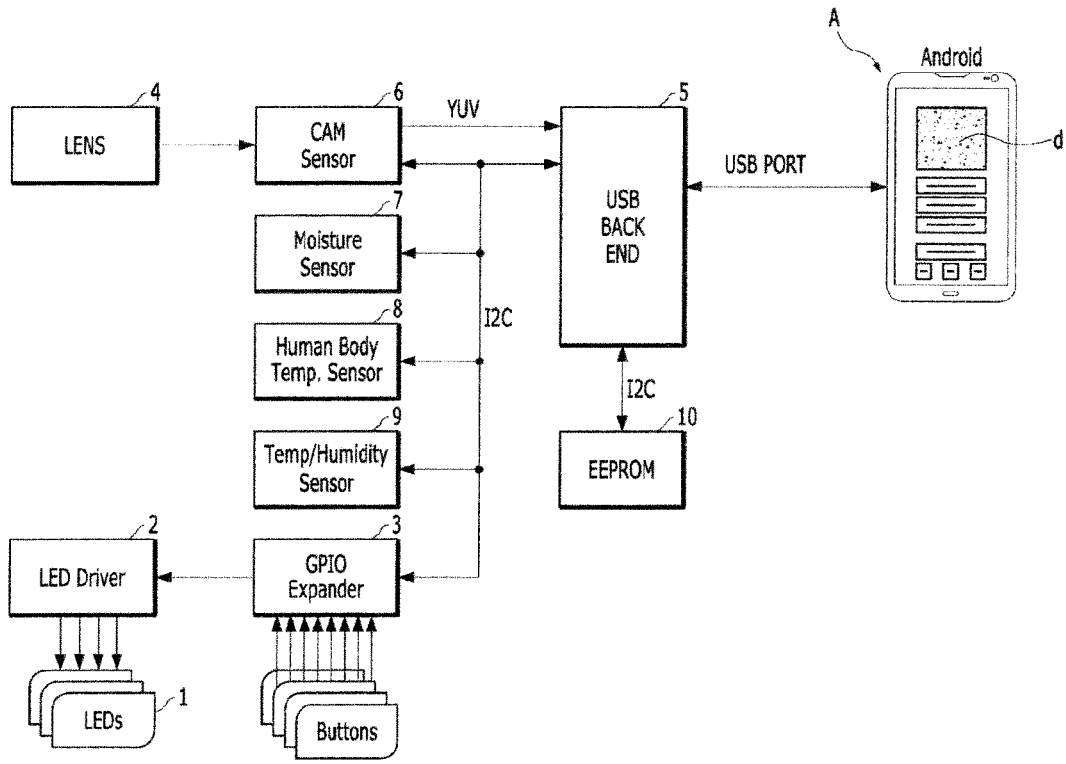
FIGS. 1a and 1b are overall block diagrams of "a device for acquiring personal health information" according to the present invention.
Figure 1B:
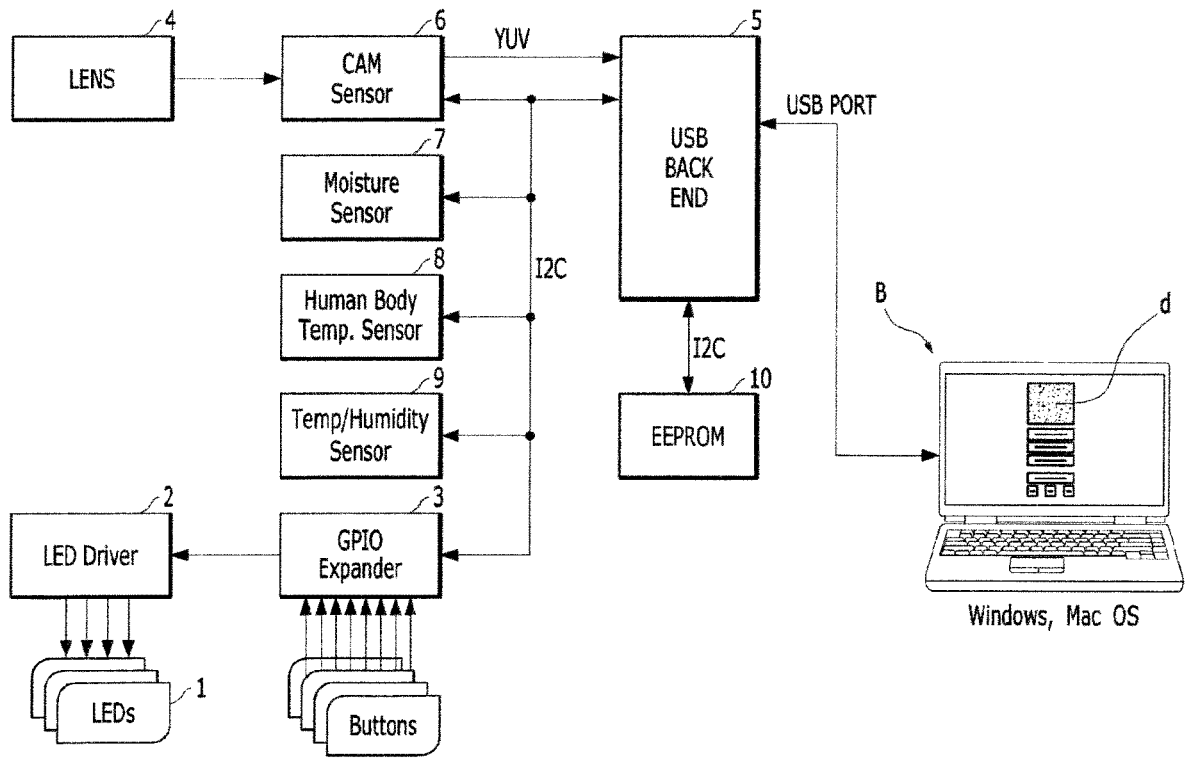

An embodiment will be described as a device for acquiring personal health information of the present invention referring to FIGS. 1a and 1b, and will be described with reference to other attached drawings as necessary.

As an image information acquiring unit for acquiring image information on any one of the skin (including the hair) image used to diagnose the skin, the nose, and the ears, and the mouth image used to diagnose the ears, the nose, and the throat, and the teeth image used to diagnose the teeth, a device for acquiring personal image information according to the present invention includes an LED light 1 for emitting light to be projected on a subject, an LED driver 2 for driving the LED light 1, a general purpose input/output (GPIO) expander 3 for controlling the LED driver 2 to turn on the LED light 1, a lens 4 for causing the light (image information) projected and reflected by the LED light 1 to be passed through, and a CAM sensor (C-MOS sensor) 6 for receiving the light (image information) passing through the lens and converting it into a YUV video signal to be transmitted to a USB back end 5.

In addition, the device includes: a moisture sensor 7 for acquiring moisture of skin with a built-in microcomputer (not shown) to cause the acquired information to be transmitted to the USB back end 5 via I2C (communication standard) communication; a human body temperature sensor 8 for acquiring body temperature of a human body to cause the acquired information to be transmitted to the USB back end 5 via I2C communication; and a temperature/humidity sensor 9 for acquiring the ambient temperature and humidity of a person who undergoes an examination, with a built-in microcomputer (not shown) to cause the acquired information to be transmitted to the USB back end 5 via I2C communication.

The device according to the present invention further includes the USB back end 5 for causing the image information received as YUV signal from the CAM sensor 6 in the image information acquiring unit and health care information received from the moisture sensor 7, the human body temperature sensor 8, and the temperature/humidity sensor 9 through an I2C communication to be converted into a USB standard signal, in which the image information and the health care information transmitted to the USB back end 5 are transmitted to a personal terminal A (Android) or a personal computer B (Windows, Mac OS) as a USB standard signal via a USB port, and an electrically erasable programmable read-only memory EEPROM 10 for communicating with the USB back end 5 via I2C communication to allow the USB back end 5 to make a correct and smooth interface between the CAM sensor 6, the moisture sensor 7, the human body temperature sensor 8, and the temperature/humidity sensor 9, and a personal terminal A and personal computer B (Windows, Mac OS) for the image information and the health care information.

As described above, according to the present invention, when each user wants to acquire image information on any one subject of the skin (including the hair), the nose, the ears, and the mouth associated with an ENT clinic, and teeth associated with a dental clinic using the image information acquiring unit, the GPIO expander 3 controls the LED driver 2 to cause LED light 1 to be emitted by pressing activation buttons, whereby the emitted illumination light is projected on the subject.

The light projected on the subject is reflected back to cause the reflected light (image information) to pass through the lens 4, and the light passing through the lens is received by the CAM sensor 6, converted into a v YUV video signal, and then transmitted to the USB back end 5.

The YUV signal transmitted from the CAM sensor 6 to the USB back end 5 is converted into a USB standard signal, transmitted to a personal terminal (Android) A or a personal computer (Windows, Mac OS) B via a USB port, and displayed as an image on the display d by operation programs in the personal terminal A or the personal computer B, to cause skin image information to be accumulated by analyzing, storing, and making the same into data.

With respect to image information on the skin of the acquired image information, sebum, pore, melanin, acne, wrinkle, and sensitivity states are analyzed by operating programs in the personal terminal A (Android) or the personal computer B (Windows, Mac OS) and the information analyzed is stored and accumulated.

In addition, the image information on the nose, the ears, and the mouth image used to diagnose the ears, the nose, and the throat, and the teeth image used to diagnose the teeth among the acquired image information, is displayed as an image by operating programs in the personal terminal (Android) or the personal computer (Windows, Mac OS), diagnosed as compared with sample image, and accumulated by storing and making the same into data.

Meanwhile, when each user wants to acquire information on any one of skin moisture, body temperature, and ambient temperature/humidity of a person who undergoes an examination, as health care information, the GPIO expander 3 allows the information to be acquired using the moisture sensor, the body temperature sensor, and the temperature/humidity sensor having a built-in microcomputer (not shown) by pressing the corresponding activation button. The acquired information is analyzed from the moisture sensor, the body temperature sensor, and the temperature/humidity sensor and transmitted to the USB back end via I2C communication, and the transmitted information is transmitted to the personal terminal A or the personal computer B through the USB port, in which the information is displayed as an image on the display d in the personal terminal A or the personal computer B, thereby storing and accumulating the health care information.

MODE FOR INVENTION

Hereinafter, preferred embodiments of the present invention will be described in detail with reference to the accompanying drawings.

With respect to FIGS. 1*a* and 1*b*, the first to seventh embodiments will be described as a device for acquiring personal health information according to the present invention and will be described with reference to other attached drawings as necessary.

First, a first embodiment will be described as a device for acquiring personal health information according to the present invention.

A device for acquiring personal image information according to the present invention includes, as an image information acquiring unit for acquiring image information on any one of the skin (including the hair) image used to diagnose the skin; the nose, the ear, and the mouth image used to diagnose the ears, the nose, and the throat; and the teeth image used to diagnose the teeth; an LED light 1 for emitting light to cause the light to be projected on a subject, an LED driver 2 for driving the LED light 1, a general purpose input/output (GPIO) expander 3 for controlling the LED driver 2 to turn on the LED light 1, a lens 4 for causing the light (image information) projected and reflected by the LED light 1 to be passed through, and a CAM sensor (C-MOS sensor) 6 for receiving the light (image information) passing through the lens and converting it into a YUV video signal to be transmitted to a USB back end 5.

In addition, the device includes a moisture sensor 7 for acquiring moisture of skin with a built-in microcomputer (not shown) to cause the acquired information to be transmitted to the USB back end 5 via I2C (communication standard) communication, a human body temperature sensor 8 for acquiring body temperature of a human body to cause the acquired information to be transmitted to the USB back end 5 via I2C communication, and a temperature/humidity sensor 9 for acquiring the ambient temperature and humidity of a person who undergoes an examination with a built-in microcomputer (not shown) to cause the acquired information to be transmitted to the USB back end 5 via I2C communication.

The device according to the present invention further includes the USB back end 5 for causing the image information received as YUV signal from the CAM sensor 6 in the image information acquiring unit and health care information received from the moisture sensor 7, the human body temperature sensor 8, and the temperature/humidity sensor 9 through an I2C communication to be converted into a USB standard signal, in which the image information and the health care information transmitted to the USB back end 5 are transmitted to a personal terminal A (Android) or a personal computer B (Windows, Mac OS) as a USB standard signal via a USB port, and an electrically erasable programmable read-only memory EEPROM 10 for communicating with the USB back end 5 via I2C communication to allow the USB back end 5 to make a correct and smooth interface between the CAM sensor 6, the moisture sensor 7, the human body temperature sensor 8, and the temperature/humidity sensor 9, and a personal terminal A and personal computer B (Windows, Mac OS) for the image information and the health care information.

Figure 2A:
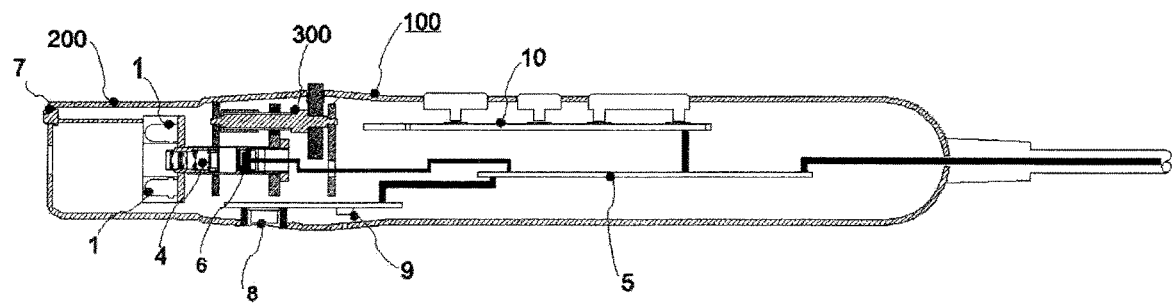
Figure 2B:
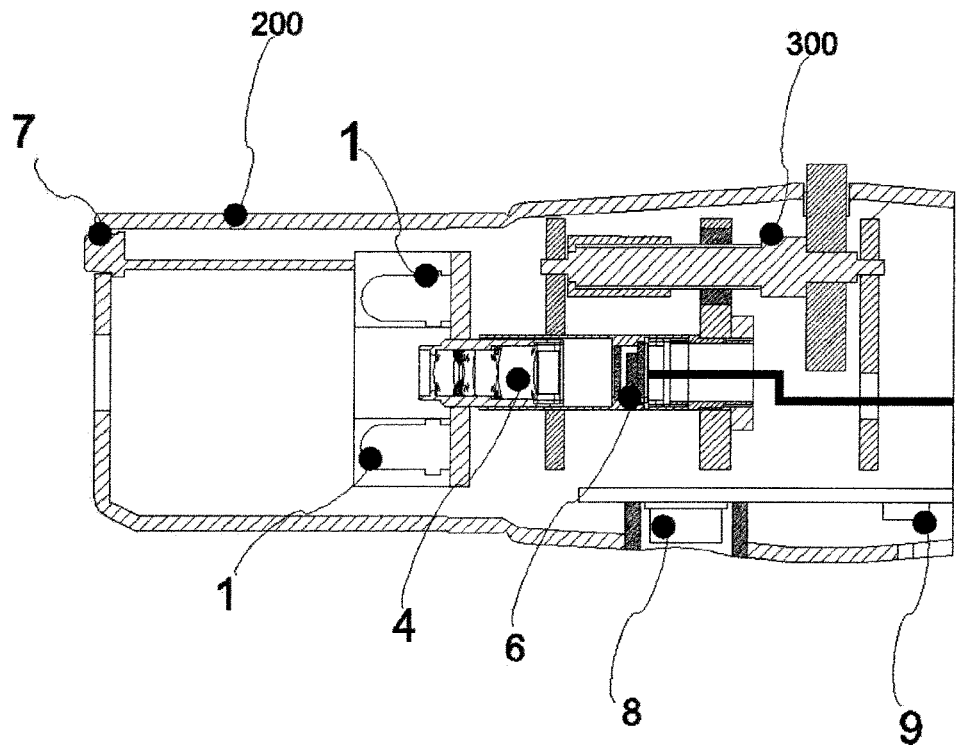

As shown in FIGS. 2a and 2b, the image information acquiring unit for acquiring the skin (including hair) image used to diagnose the skin is configured such that: a front portion of a front head 200 of a device body 100 may have a planar shape and a certain area so as to be contact with the skin of a person who undergoes an examination and thereby easily obtain health information on the skin; an LED light 1, a lens 4, and a CAM sensor 6 are sequentially arranged inside the head 200 and the device body 100; the USB back end 5 is provided in a rear portion of the CAM sensor 6; and a EEPROM 10 is provided above the USB back end 5 together with activation buttons.

A humidity sensor 7 is disposed on one side of the front portion of the front head 200, a human body temperature sensor 8 and a temperature/humidity sensor 9 are disposed on one side of the device body 100, and a focus adjustment function means 300 for adjusting a focus of the CAM sensor 6 is provided.

Figure 3A:
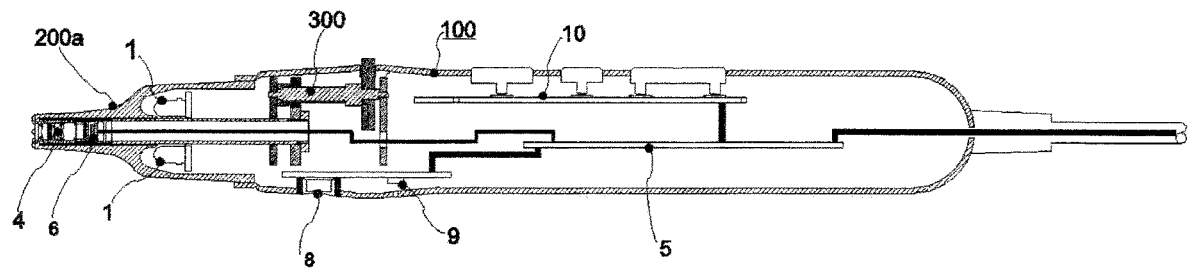
Figure 3B:
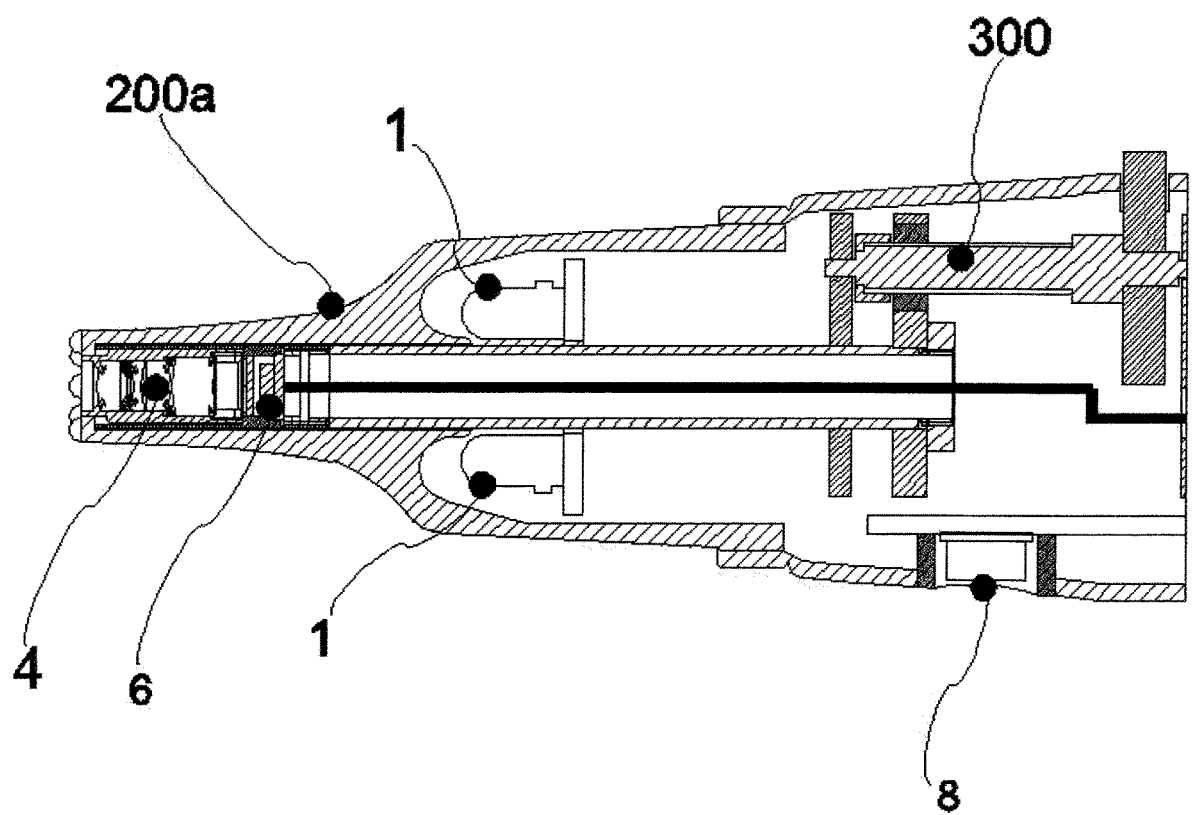

As shown in FIGS. 3a and 3b, the image information acquiring unit for acquiring image information on the nose, the ears, and the mouth image used to diagnose the ears, the nose, and the throat is configured such that a front head 200a of the device body 100 is funnel-shaped with a transparent body to easily obtain health information from the nose, the ears, and the mouth of a person who undergoes an examination; a lens 4 and a CAM sensor 6 are formed at a front tip end of the front head 200a; an LED light 1 is arranged in a rear portion of the CAM sensor 6; a USB back end 5 is arranged in a rear portion of the LED light 1; and a EEPROM 10 is provided above the USB back end 5 together with activation buttons.

In addition, a human body temperature sensor 8 and a temperature/humidity sensor 9 are provided in one side of the device body 100, and a focus adjustment function unit 300 is provided to adjust a focus of the CAM sensor 6.

Figure 4A:
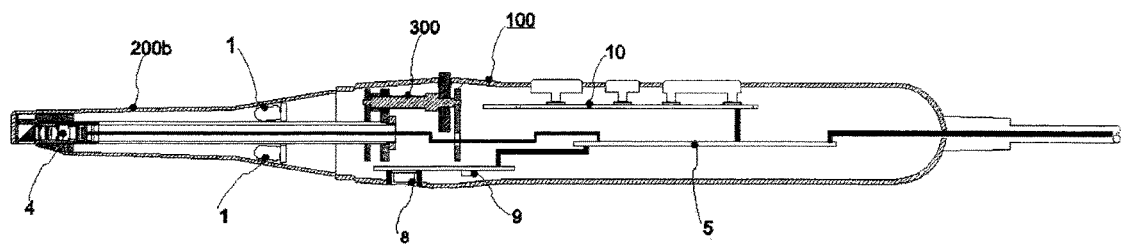
Figure 4B:
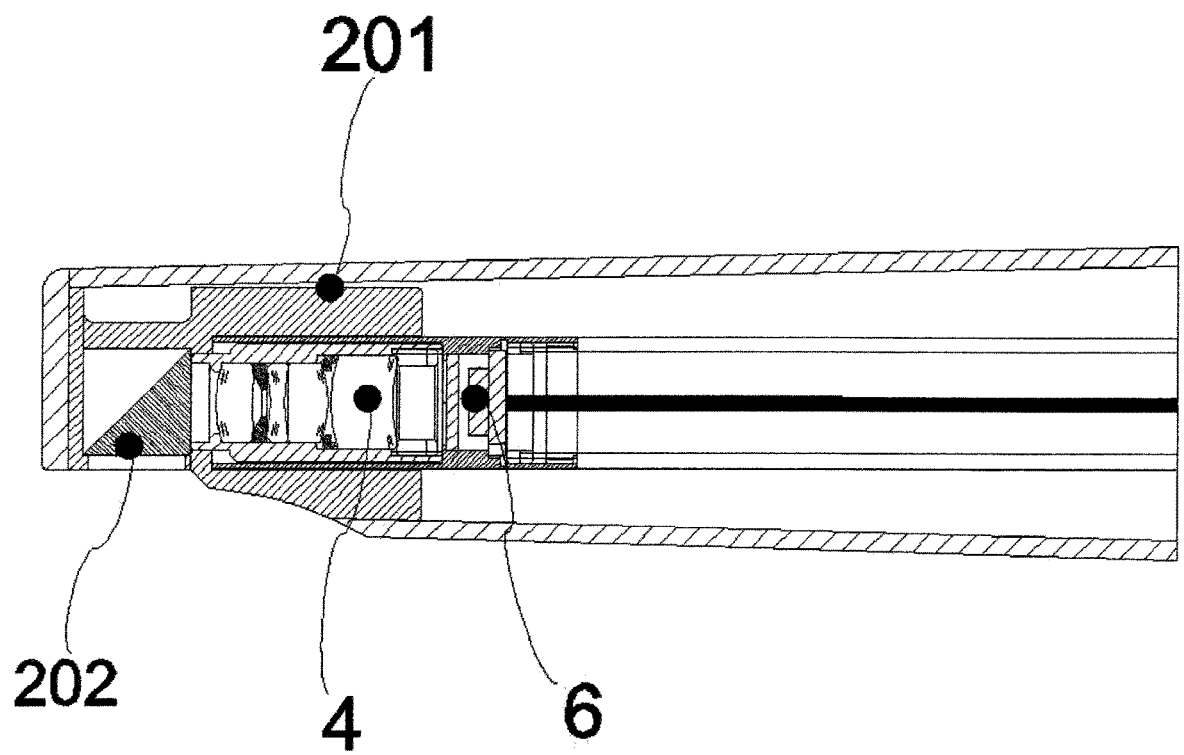

As shown in FIGS. 4a and 4b, the image information acquiring unit for acquiring the teeth image used to diagnose the teeth is configured such that a front head 200b of a device body 100 is funnel-shaped so as to easily obtain health information from the teeth of a person who undergoes an examination; the front head 200b that is funnel-shaped includes a transparent prism 201 that is transparent and irradiates subject with light and a light-receiving prism 202 that receives light from the subject; a lens 4, a CAM sensor 6, and an LED light 1 are sequentially provided in a rear portion of the light-receiving prism 202; the USB back end 5 is provided in a rear portion of the LED light 1; and EEPROM 10 is provided above the USB back end 5 together with activation buttons.

In addition, a human body temperature sensor 8 and a temperature/humidity sensor 9 are provided in one side of the device body 100, and a focus adjustment function unit 300 is provided to adjust a focus of the CAM sensor 6.

As described above, according to the present invention, when each user wants to acquire image information on any one subject of the skin (including the hair), the nose, the ears, and the mouth associated with an ENT clinic, and teeth associated with a dental clinic using the image information acquiring unit, the GPIO expander 3 controls the LED driver 2 to cause LED light 1 to be emitted by pressing activation buttons, whereby the emitted illumination light is projected on the subject.

The light projected on the subject is reflected back to cause the reflected light (image information) to pass through the lens 4, and the light passing through the lens is received by the CAM sensor 6, converted into a YUV video signal, and then transmitted to the USB back end 5.

The YUV signal transmitted from the CAM sensor 6 to the USB back end 5 is converted into a USB standard signal, transmitted to a personal terminal (Android) A or a personal computer (Windows, Mac OS) B via a USB port, and displayed as an image on the display d by operation programs in the personal terminal A or the personal computer B, to cause the skin image information to be accumulated by analyzing, storing, and making the same into data.

With respect to information on the skin image of the acquired image information, such as the state of sebum, pores, melanin, acne, wrinkles, and sensitivity are analyzed by operating programs in the personal terminal A (Android) or the personal computer B (Windows, Mac OS) and the information analyzed is stored and accumulated.

In addition, image information on the nose, the ears, and the mouth image used to diagnose the ears, the nose, and the throat, and the teeth image used to diagnose the teeth among the acquired image information, is displayed as an image by operating programs in the personal terminal (Android) or the personal computer (Windows, Mac OS), diagnosed as compared with sample image, and accumulated by storing and making the same into data.

Meanwhile, when each user wants to acquire information on any one of skin moisture, body temperature, and ambient temperature/humidity of a person who undergoes an examination as health care information, the GPIO expander 3 allows the information to be acquired using the moisture sensor, the body temperature sensor, and the temperature/humidity sensor having a built-in microcomputer (not shown) by pressing the corresponding activation button, and the acquired information to be analyzed from the moisture sensor, the body temperature sensor, and the temperature/humidity sensor and transmitted to the USB back end via I2C communication, whereby the transmitted information is transmitted to the personal terminal A or the personal computer B through the USB port, in which the information is displayed as an image on the display d in the personal terminal A or the personal computer B, thereby storing and accumulating the health care information.

The device for acquiring personal health information according to the present invention is capable of easily and periodically acquiring, anytime and anywhere or without regard to place and time, information on ambient temperature/humidity and health information of an individual, such as state of the skin (including the hair), the nose, the ears, and the mouth associated with an ENT clinic, and the teeth associated with a dental clinic, skin moisture, and body temperature through image information having multiple functions and a multifunctional health care sensor, enabling the acquired health information to be accumulated over a long time in a personal terminal (Android) or a personal computer (PC) by analyzing, storing, and making the same into data, and diagnosed and treated as necessary, and continuously managing the periodically accumulated personal health information such that the personal health information can be used as critical information by which a disease cause and the like can be fundamentally understood during an incidence of a disease in the future.

In other words, by accumulating continuously personal health information such as a state of skin (including the hair), the nose, the ears, and the mouth associated with an ENT clinic, and the teeth associated with a dental clinic, skin moisture, body temperature, and ambient temperature/humidity over a long period of time, a disease cause may be fundamentally understood during an incidence of a disease in the future; each user may analyze and diagnose oneself according to the user's own operating programs as necessary in order not to miss a time when the user must be treated by a specialist; and in particular, information on the skin such as the state of sebum, pores, melanin, acne, wrinkles, sensitivity, and moisture is continuously and periodically acquired from the skin over a long period of time to enable the acquired information to be accumulated by analyzing, storing, and making the same into data, whereby a correct cosmetic prescription can be made and management plan or treatment method or information such as cosmetics suitable for the skin can be provided when a skin disease occurs or when selecting a cosmetic.

The second to seventh embodiments of the present invention will now be described.

In the description of the second to seventh embodiments of the present invention, the detailed description of the image information acquiring unit is based on the description of the first embodiment.

A device for acquiring personal image information according to the present invention includes, as an image information acquiring unit for acquiring image information on any one image of the skin (including the hair) image used to diagnose the skin, the nose, and the ear, and mouth image used to diagnose the ears, the nose, and the throat, and teeth image used to diagnose the teeth, an LED light 1 for emitting light to cause the light to be projected on a subject, an LED driver 2 for driving the LED light 1, a general purpose input/output (GPIO) expander 3 for controlling the LED driver 2 to turn on the LED light 1, a lens 4 for causing the light (image information) projected and reflected by the LED light 1 to be passed through, and a CAM sensor (C-MOS sensor) 6 for receiving the light (image information) passing through the lens and converting it into a YUV video signal to be transmitted to a USB back end 5.

In addition, the device includes a moisture sensor 7 for acquiring moisture of skin with a built-in microcomputer (not shown) to cause the acquired information to be transmitted to the USB back end 5 via I2C (communication standard) communication, and a human body temperature sensor 8 for acquiring body temperature of a human body to cause the acquired information to be transmitted to the USB back end 5 via I2C communication.

The device according to the present invention further includes the USB back end 5 for causing the image information received as YUV signal from the CAM sensor 6 in the image information acquiring unit and health care information received from the moisture sensor 7 and the human body temperature sensor 8 through an I2C communication to be converted into a USB standard signal, in which the image information and the health care information transmitted to the USB back end 5 are transmitted to a personal terminal A (Android) or a personal computer B (Windows, Mac OS) as a USB standard signal via a USB port, and an electrically erasable programmable read-only memory EEPROM 10 for communicating with the USB back end 5 via I2C communication to allow the USB back end 5 to make a correct and smooth interface between the CAM sensor 6, the moisture sensor 7, and the human body temperature sensor 8, and a personal terminal A and personal computer B (Windows, Mac OS) for the image information and the health care information.

Meanwhile, when each user wants to acquire any one of skin moisture and body temperature as health care information, the GPIO expander 3 allows the information to be acquired using the moisture sensor 7 and the body temperature sensor 8 having a built-in microcomputer (not shown) by pressing the corresponding activation button, and the acquired information to be analyzed from the moisture sensor 7 and the body temperature sensor 8 and transmitted to the USB back end via I2C communication, whereby the transmitted information is transmitted to the personal terminal A or the personal computer B through the USB port, in which the information is displayed as an image on the display d in the personal terminal A or the personal computer B, thereby storing and accumulating the health care information.

A device for acquiring personal image information according to a third embodiment of the present invention includes, as an image information acquiring unit for acquiring image information on any one of the skin (including the hair) image used to diagnose the skin; the nose, the ear, and the mouth image used to diagnose the ears, nose, and throat; and the teeth image used to diagnose the teeth, an LED light 1 for emitting light to cause it to be projected on a subject, an LED driver 2 for driving the LED light 1, a general purpose input/output (GPIO) expander 3 for controlling the LED driver 2 to turn on the LED light 1, a lens 4 for causing the light (image information) projected and reflected by the LED light 1 to be passed through, and a CAM sensor (C-MOS sensor) 6 for receiving the light (image information) passing through the lens and converting it into a YUV video signal to be transmitted to a USB back end 5.

In addition, the device includes a moisture sensor 7 for acquiring moisture of skin with a built-in microcomputer (not shown) to cause the acquired information to be transmitted to the USB back end 5 via I2C (communication standard) communication, and a temperature/humidity sensor 9 for acquiring the ambient temperature and humidity of a person who undergoes an examination with a built-in microcomputer (not shown) to cause the acquired information to be transmitted to the USB back end 5 via I2C communication.

The device according to the present invention further includes the USB back end 5 for causing the image information received as YUV signal from the CAM sensor 6 in the image information acquiring unit and health care information received from the moisture sensor 7 and the temperature/humidity sensor 9 through an I2C communication to be converted into a USB standard signal, in which the image information and the health care information transmitted to the USB back end 5 is transmitted to a personal terminal A (Android) or a personal computer B (Windows, Mac OS) as a USB standard signal via a USB port, and an electrically erasable programmable read-only memory EEPROM 10 for communicating with the USB back end 5 via I2C communication to allow the USB back end 5 to make a correct and smooth interface between the CAM sensor 6, the moisture sensor 7, and the temperature/humidity sensor 9, and a personal terminal A and personal computer B (Windows, Mac OS) for the image information and the health care information.

Meanwhile, when each user wants to acquire any one of skin moisture and ambient temperature/humidity of a person who undergoes an examination as health care information, the GPIO expander 3 allows the information to be acquired using the moisture sensor 7, and the temperature/humidity sensor 9 having a built-in microcomputer (not shown) by pressing the corresponding activation button, and the acquired information to be analyzed from the moisture sensor and the temperature/humidity sensor and transmitted to the USB back end via I2C communication, whereby the transmitted information is transmitted to the personal terminal A or the personal computer B through the USB port, in which the information is displayed as an image on the display d in the personal terminal A or the personal computer B, thereby storing and accumulating the health care information.

A device for acquiring personal image information according to a fourth embodiment of the present invention includes, as an image information acquiring unit for acquiring image information on any one of the skin (including the hair) image used to diagnose the skin; the nose, the ear, and the mouth image used to diagnose the ears, the nose, and the throat; and the teeth image used to diagnose the teeth, an LED light 1 for emitting light to cause the light to be projected on a subject, an LED driver 2 for driving the LED light 1, a general purpose input/output (GPIO) expander 3 for controlling the LED driver 2 to turn on the LED light 1, a lens 4 for causing the light (image information) projected and reflected by the LED light 1 to be passed through, and a CAM sensor (C-MOS sensor) 6 for receiving the light (image information) passing through the lens and converting it into a YUV video signal to be transmitted to a USB back end 5.

In addition, the device includes a human body temperature sensor 8 for acquiring body temperature of a human body to cause the acquired information to be transmitted to the USB back end 5 via I2C communication, and a temperature/humidity sensor 9 for acquiring the ambient temperature and humidity of a person who undergoes an examination with a built-in microcomputer (not shown) to cause the acquired information to be transmitted to the USB back end 5 via I2C communication.

The device according to the present invention further includes the USB back end 5 for causing the image information received as YUV signal from the CAM sensor 6 in the image information acquiring unit and health care information received from the human body temperature sensor 8 and the temperature/humidity sensor 9 through an I2C communication to be converted into a USB standard signal, in which the image information and the health care information transmitted to the USB back end 5 are transmitted to a personal terminal A (Android) or a personal computer B (Windows, Mac OS) as a USB standard signal via a USB port, and an electrically erasable programmable read-only memory EEPROM 10 for communicating with the USB back end 5 via I2C communication to allow the USB back end 5 to make a correct and smooth interface between the CAM sensor 6, the human body temperature sensor 8, and the temperature/humidity sensor 9, and a personal terminal A and personal computer B (Windows, Mac OS) for the image information and the health care information.

Meanwhile, when each user wants to acquire any one of body temperature of a human body and ambient temperature/humidity of a person who undergoes an examination as health care information, the GPIO expander 3 allows the information to be acquired using the body temperature sensor 8 and the temperature/humidity sensor 9 having a built-in microcomputer (not shown) by pressing the corresponding activation button, and the acquired information to be analyzed from the body temperature sensor 8 and the temperature/humidity sensor 9 and transmitted to the USB back end via I2C communication, whereby the transmitted information is transmitted to the personal terminal A or the personal computer B through the USB port, in which the information is displayed as an image on the display d in the personal terminal A or the personal computer B, thereby storing and accumulating the health care information.

A device for acquiring personal image information according to a fifth embodiment of the present invention includes, as an image information acquiring unit for acquiring image information on any one of the skin (including the hair) image used to diagnose the skin; the nose, the ear, and the mouth image used to diagnose the ears, the nose, and the throat; and the teeth image used to diagnose the teeth, an LED light 1 for emitting light to cause the light to be projected on a subject, an LED driver 2 for driving the LED light 1, a general purpose input/output (GPIO) expander 3 for controlling the LED driver 2 to turn on the LED light 1, a lens 4 for causing the light (image information) projected and reflected by the LED light 1 to be passed through, and a CAM sensor (C-MOS sensor) 6 for receiving the light (image information) passing through the lens and converting it into a YUV video signal to be transmitted to a USB back end 5.

In addition, the device includes a moisture sensor 7 for acquiring moisture of skin with a built-in microcomputer (not shown) to cause the acquired information to be transmitted to the USB back end 5 via I2C (communication standard) communication.

The device according to the present invention further includes the USB back end 5 for causing the image information received as YUV signal from the CAM sensor 6 in the image information acquiring unit and health care information received from the moisture sensor 7 through an I2C communication to be converted into a USB standard signal, in which the image information and the health care information transmitted to the USB back end 5 are transmitted to a personal terminal A (Android) or a personal computer B (Windows, Mac OS) as a USB standard signal via a USB port, and an electrically erasable programmable read-only memory EEPROM 10 for communicating with the USB back end 5 via I2C communication to allow the USB back end 5 to make a correct and smooth interface between the CAM sensor 6 and the moisture sensor 7, and a personal terminal A and personal computer B (Windows, Mac OS) for the image information and the health care information.

Meanwhile, when each user wants to acquire moisture of the skin as health care information, the GPIO expander 3 allows the information to be acquired using the moisture sensor 7 having a built-in microcomputer (not shown) by pressing the corresponding activation button, and the acquired information to be analyzed from the moisture sensor 7 and transmitted to the USB back end via I2C communication, whereby the transmitted information is transmitted to the personal terminal A or the personal computer B through the USB port, in which the information is displayed as an image on the display d in the personal terminal A or the personal computer B, thereby storing and accumulating the health care information.

Further, a device for acquiring personal image information according to a sixth embodiment of the present invention includes, as an image information acquiring unit for acquiring image information on any one of the skin (including the hair) image used to diagnose the skin; the nose, the ear, and the mouth image used to diagnose the ears, the nose, and the throat; and the teeth image used to diagnose the teeth, an LED light 1 for emitting light to cause the light to be projected on a subject, an LED driver 2 for driving the LED light 1, a general purpose input/output (GPIO) expander 3 for controlling the LED driver 2 to turn on the LED light 1, a lens 4 for causing the light (image information) projected and reflected by the LED light 1 to be passed through, and a CAM sensor (C-MOS sensor) 6 for receiving the light (image information) passing through the lens and converting it into a YUV video signal to be transmitted to a USB back end 5.

In addition, the device includes a human body temperature sensor 8 for acquiring body temperature of a human body with a built-in microcomputer (not shown) to cause the acquired information to be transmitted to the USB back end 5 via I2C (communication standard) communication.

The device according to the present invention further includes the USB back end 5 for causing the image information received as YUV signal from the CAM sensor 6 in the image information acquiring unit and health care information received from the human body temperature sensor 8 through an I2C communication to be converted into a USB standard signal, in which the image information and the health care information transmitted to the USB back end 5 are transmitted to a personal terminal A (Android) or a personal computer B (Windows, Mac OS) as a USB standard signal via a USB port, and an electrically erasable programmable read-only memory EEPROM 10 for communicating with the USB back end 5 via I2C communication to allow the USB back end 5 to make a correct and smooth interface between the CAM sensor 6 and the human body temperature sensor 8, and a personal terminal A and personal computer B (Windows, Mac OS) for the image information and the health care information.

Meanwhile, when each user wants to acquire body temperature of a human body as health care information, the GPIO expander 3 allows the information to be acquired using the body temperature sensor 8 having a built-in microcomputer (not shown) by pressing the corresponding activation button, and the acquired information to be analyzed from the body temperature sensor 8 and transmitted to the USB back end via I2C communication, and the transmitted information is transmitted to the personal terminal A or the personal computer B through the USB port, in which the information is displayed as an image on the display d in the personal terminal A or the personal computer B, thereby storing and accumulating the health care information.

Further, a device for acquiring personal image information according to a seventh embodiment of the present invention includes, as an image information acquiring unit for acquiring image information on any one of the skin (including the hair) image used to diagnose the skin; the nose, the ear, and the mouth image used to diagnose the ears, the nose, and the throat; and the teeth image used to diagnose the teeth, an LED light 1 for emitting light to cause the light to be projected on a subject, an LED driver 2 for driving the LED light 1, a general purpose input/output (GPIO) expander 3 for controlling the LED driver 2 to turn on the LED light 1, a lens 4 for causing the light (image information) projected and reflected by the LED light 1 to be passed through, and a CAM sensor (C-MOS sensor) 6 for receiving the light (image information) passing through the lens and converting it into a YUV video signal to be transmitted to a USB back end 5.

In addition, the device includes a temperature/humidity sensor 9 for acquiring the ambient temperature and humidity of a person who undergoes an examination with a built-in microcomputer (not shown) to cause the acquired information to be transmitted to the USB back end 5 via I2C communication.

The device according to the present invention further includes the USB back end 5 for causing the image information received as YUV signal from the CAM sensor 6 in to the image information acquiring unit and health care information received from the temperature/humidity sensor 9 through an I2C communication to be converted into a USB standard signal, and an electrically erasable programmable read-only memory EEPROM 10 for causing the image information and the health care information transmitted to the USB back end 5 to be transmitted to a personal terminal A (Android) or a personal computer B (Windows, Mac OS) as a USB standard signal via a USB port and communicating with the USB back end 5 via I2C communication to allow the USB back end 5 to make a correct and smooth interface between the CAM sensor 6 and the temperature/humidity sensor 9, and the personal terminal A and the personal computer B (Windows, Mac OS) for the image information and the health care information.

Meanwhile, when each user wants to acquire ambient temperature/humidity of a person who undergoes an examination as health care information, the GPIO expander 3 allows the information to be acquired using the temperature/humidity sensor 9 having a built-in microcomputer (not shown) by pressing the corresponding activation button, and the acquired information to be analyzed from the temperature/humidity sensor 9 and transmitted to the USB back end via I2C communication, whereby the transmitted information is transmitted to the personal terminal A or the personal computer B through the USB port, in which the information is displayed as an image on the display d in the personal terminal A or the personal computer B, thereby storing and accumulating the health care information.

Hereinafter, eighth to tenth embodiments will be described as a method for acquiring personal health information in order to achieve the object of the present invention.

Figure 5:
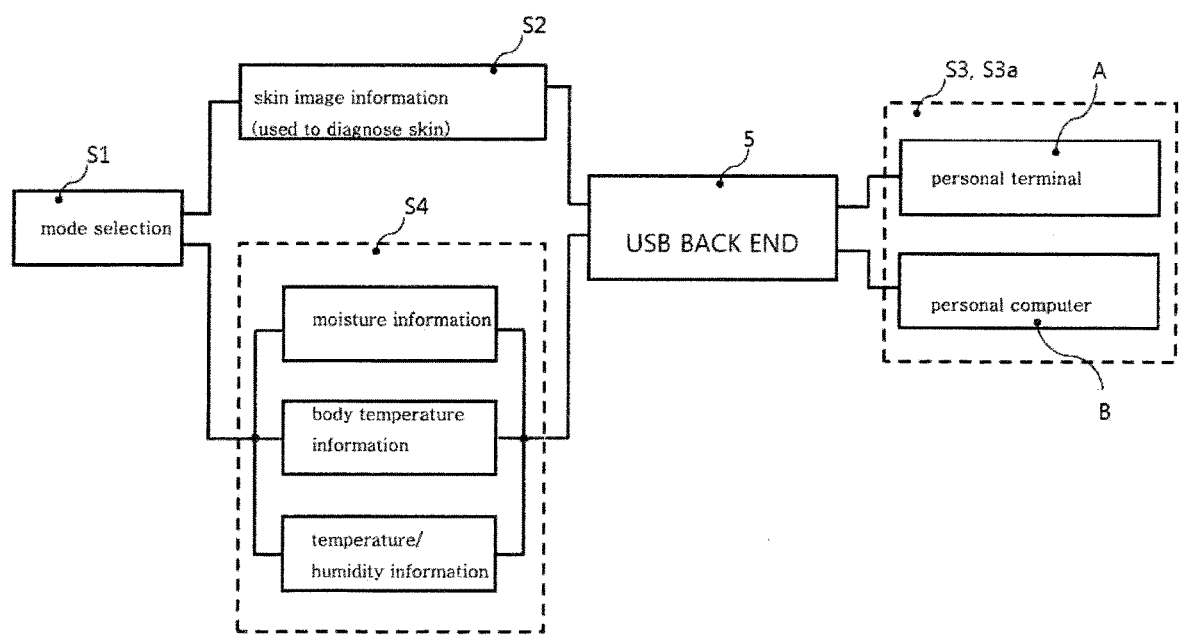
FIG. 5 is a block diagram of a method for acquiring skin image information and health care information according to the present invention.

First, an eighth embodiment of the present invention will be described with reference to FIG. 5, and will be described with reference to FIGS. 1a to 1b and 2a to 2b as necessary.

Step 1—As a mode selection step S1, by pressing activation buttons, a general purpose input output (GPIO) expander 3 is allowed to select a mode for acquiring desired information of skin (including hair) image information as personal health information, and skin moisture, body temperature, and ambient temperature and humidity of a person who undergoes an examination as health care information.

Step 2—As a step S2 of acquiring the image information on the skin, when the skin (including the hair) image information is selected according to mode selection in the mode selection step, an LED light 1 is emitted to the skin desired to acquire the health information to cause the light to be projected, the skin image reflected from the skin is received by a CAM sensor 6 through a lens 4, and the received image information is converted into an image signal YUV signal and transmitted to a USB back end 5.

That is, when each user presses the activation buttons to acquire image information on the skin (including hair), the GPIO expander 3 is allowed to control the LED driver 2, whereby the LED light 1 is emitted to cause the emitted light to be projected on the skin, the light projected on the skin is reflected back to cause the reflected light (image information) to pass through the lens 4, and the light passing through the lens is received by the CAM sensor 6, converted into a video signal of YUV signal, and then transmitted to the USB back end 5, thereby acquiring the skin image information.

Step 3—As a storage step S3, the YUV signal is converted into a USB standard signal in the USB back end 5, transmitted to a personal terminal A or a personal computer B via a USB port, and displayed as an image on a display in the personal terminal A or the personal computer B, to cause the skin image information acquired to be accumulated by analyzing, storing, and making the same into data.

In other words, the YUV signal transmitted from the CAM sensor 6 to the USB back end 5 is converted into a USB standard signal, transmitted to a personal terminal (Android) A or a personal computer (Windows, Mac OS) B via a USB port, and displayed as an image on the display by operation programs in the personal terminal A or the personal computer B, to cause the skin image information to be accumulated by analyzing, storing, and making the same into data.

With respect to information on the skin of the acquired image information, sebum, pore, melanin, acne, wrinkle, and sensitivity states are analyzed by operating programs in the personal terminal A (Android) or the personal computer B (Windows, Mac OS) and the information analyzed is stored and accumulated.

Step 4—As a step S4 of acquiring the health care information, when selecting a mode for acquiring desired information of skin moisture, body temperature, and ambient temperature and humidity of the person who undergoes an examination as health care information in the mode selection step, information is acquired using a moisture sensor 7, a human body temperature sensor 8, and a temperature/humidity sensor 9 having built-in microcomputer, and the acquired information is analyzed from the moisture sensor 7, the human body temperature sensor 8, and the temperature/humidity sensor 9 and transmitted to the USB back end 5 via I2C communication, thereby acquiring health care information.

Step 5—As a completion step S3a, the health care information transmitted to the USB back end 5 is transmitted to the personal terminal A or the personal computer B via the USB port and is displayed as an image on a display in the personal terminal A or the personal B, thereby causing the health care information acquired to be accumulated by storing or making the same into data and completing the method.

The method for acquiring the personal health information according to the present invention is capable of easily and periodically acquiring, anytime and anywhere or without regard to place and time, information on ambient temperature/humidity and health information of an individual, such as the skin (including the hair) image, skin moisture, and body temperature through image information having multiple functions and a multifunctional health care sensor, enabling the acquired health information to be accumulated over a long time in a personal terminal (Android) or a personal computer (PC) by analyzing, storing, and making the same into data, and diagnosed and treated as necessary, and continuously managing the periodically accumulated personal health information of a user such that the personal health information can be used as critical information by which a disease cause and the like can be fundamentally understood during an incidence of a disease in the future.

Figure 6:
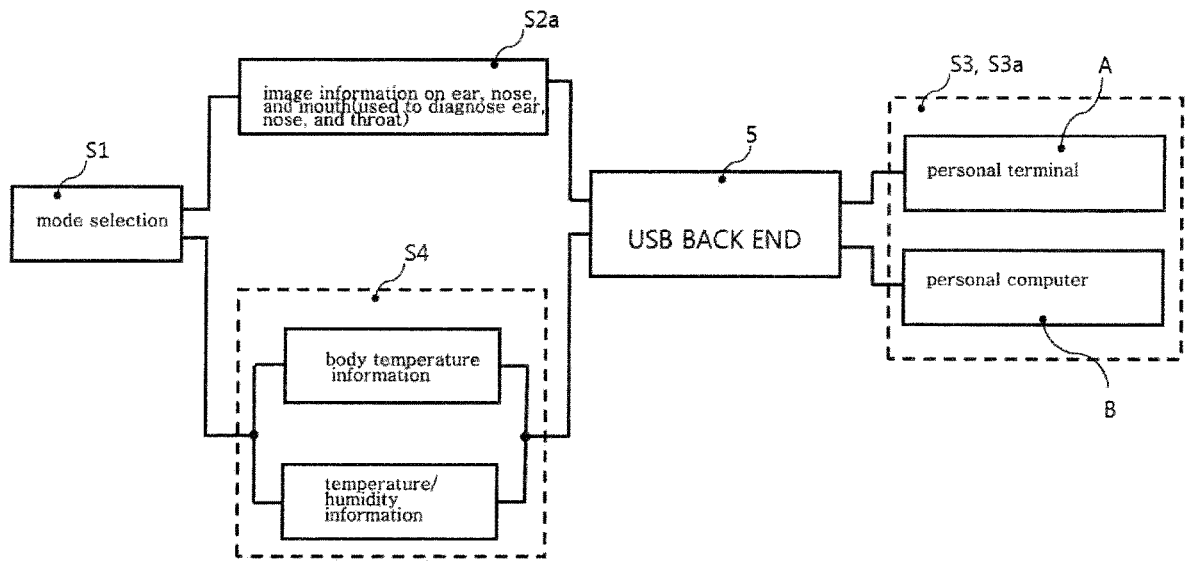
FIG. 6 is a block diagram of a method for acquiring image information on the nose, the ears, and the mouth and health care information according to the present invention.

A ninth embodiment of the present invention will be described with reference to FIG. 6, and will be also described with reference to FIGS. 1a to 1b and 3a to 3b as necessary.

Step 1—As a mode selection step S1, by pressing activation buttons, a general purpose input output (GPIO) expander 3 is allowed to select a mode for acquiring desired information of image information on the nose, the ear, and the mouth image used to diagnose the nose, the ears, and the throat as personal health information, and body temperature, and ambient temperature and humidity of a person who undergoes an examination as health care information.

Step 2—As a step S2a of acquiring the image information on the nose, the ear, and the mouth image used to diagnose the nose, the ears, and the throat, when image information on the nose, the ears, and the mouth image used to diagnose the nose, the ears, and the throat is selected according to mode selection in the mode selection step, an LED light 1 is emitted to a subject of the nose, the ears, and the mouth desired to acquire the health information, to cause the light to be projected thereon, the skin image reflected from the subject is received by a CAM sensor 6 through a lens 4, and the received image information is converted into an image signal YUV signal and transmitted to a USB back end 5.

That is, when each user presses the activation buttons to acquire image information on the nose, the ears, and the mouth, the GPIO expander 3 is allowed to control the LED driver 2, whereby the LED light 1 is emitted to cause the emitted light to be projected on the subject, the light projected on the subject is reflected back to cause the reflected light (image information) to pass through the lens 4, and the light passing through the lens is received by the CAM sensor 6, converted into a video signal of YUV signal, and then transmitted to the USB back end 5, thereby acquiring the image information on the nose, the ears, and the mouth.

Step 3—As a storage step S3, the YUV signal is converted into a USB standard signal in the USB back end 5, transmitted to a personal terminal A or a personal computer B via a USB port, displayed as an image on a display in the personal terminal A or the personal computer B, and diagnosed as compared with sample image, to cause the image information acquired to be accumulated by analyzing, storing, and making the same into data.

Step 4—As a step S4 of acquiring the health care information, when selecting a mode for acquiring desired information of body temperature, and ambient temperature and humidity of the person who undergoes an examination as health care information in the mode selection step, the information is acquired using a human body temperature sensor 8 and a temperature/humidity sensor 9 having built-in microcomputer, and the acquired information is analyzed from the human body temperature sensor 8 and the temperature/humidity sensor 9 and transmitted to the USB back end 5 via I2C communication, thereby acquiring health care information.

Step 5—As a completion step S3a, the health care information transmitted to the USB back end 5 is transmitted to the personal terminal A or the personal computer B via the USB port and is displayed as an image on a display in the personal terminal A or the personal computer B, thereby causing the health care information acquired to be accumulated by storing or making the same into data and completing the method.

The method for acquiring the personal health information according to the present invention is capable of easily and periodically acquiring, anytime and anywhere or without regard to place and time, health image information such as the nose, the ear, and the mouth image, and body temperature, and ambient temperature/humidity, enabling the acquired health information to be accumulated over a long time by operating programs in a personal terminal (Android) or a personal computer (PC) by analyzing, storing, and making the same into data, and to be diagnosed and treated as necessary, and continuously managing the periodically accumulated personal health information of a user such that the personal health information can be used as critical information by which a disease cause and the like can be fundamentally understood during an incidence of a disease in the future.

Figure 7:
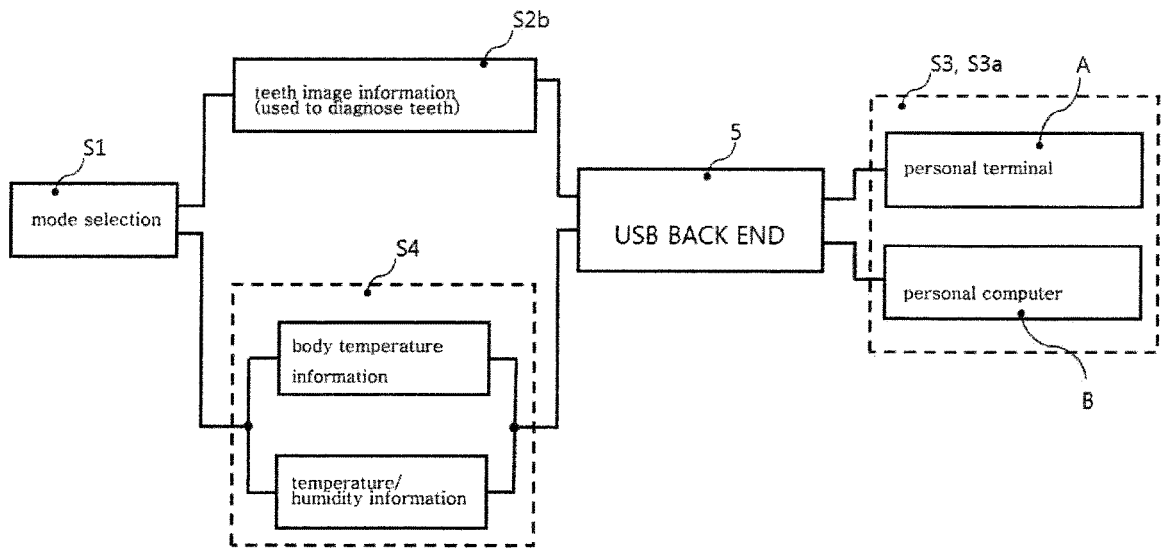
FIG. 7 is a block diagram of a method for acquiring teeth image information and health care information according to the present invention.

A tenth embodiment of the present invention will be described with reference to FIG. 7, and will be also described with reference to FIGS. 1a to 1b and 5a to 5b as necessary.

Step 1—As a mode selection step S1, by pressing activation buttons, a general purpose input output (GPIO) expander 3 is allowed to select a mode for acquiring desired information of image information on the teeth, and health care information and ambient temperature and humidity of a person who undergoes an examination as personal health information.

Step 2—As a step S2b of acquiring the image information on the teeth, when the image information on the teeth is selected according to mode selection in the mode selection step, an LED light 1 is emitted to the subject of the teeth desired to acquire the health information to cause the light to be projected thereon, the light (image information) reflected from the subject is received by a CAM sensor 6 through a lens 4, and the received image information is converted into an image signal YUV signal and transmitted to a USB back end 5.

That is, when each user presses the activation buttons to acquire image information on the teeth, the GPIO expander 3 is allowed to control the LED driver 2, whereby the LED light 1 is emitted to cause the emitted light to be projected on the subject, the light projected on the subject is reflected back to cause the reflected light (image information) to pass through the lens 4, and the light passing through the lens is received by the CAM sensor 6, converted into a video signal of YUV signal, and then transmitted to the USB back end 5, thereby acquiring the image information on the teeth.

Step 3—As a storage step S3, the YUV signal is converted into a USB standard signal in the USB back end 5, transmitted to a personal terminal A or a personal computer B via a USB port, displayed as an image on a display in the personal terminal A or the personal computer B, and to be diagnosed as compared with sample image, to cause the image information acquired to be accumulated by analyzing, storing, and making the same into data.

Step 4—As a step S4 of acquiring the health care information, when selecting a mode for acquiring desired information of body temperature, and ambient temperature and humidity of the person who undergoes an examination as health care information in the mode selection step, the information is acquired using a human body temperature sensor 8 and a temperature/humidity sensor 9 having built-in microcomputer, and the acquired information is analyzed from the human body temperature sensor 8 and the temperature/humidity sensor 9 and transmitted to the USB back end 5 via I2C communication, thereby acquiring health care information.

Step 5—As a completion step S3a, the health care information transmitted to the USB back end 5 is transmitted to the personal terminal A or the personal computer B via the USB port and is displayed as an image on a display in the personal terminal A or the personal computer B, thereby causing the health care information acquired to be accumulated by storing or making the same into data and completing the method.

The method for acquiring the personal health information according to the present invention is capable of easily and periodically acquiring, anytime and anywhere or without regard to place and time, health information of the teeth image, body temperature, and ambient temperature/humidity, enabling the acquired health information to be accumulated over a long time by operating programs in a personal terminal (Android) or a personal computer (PC) by analyzing, storing, and making the same into data, and to be diagnosed and treated as necessary, and continuously managing the periodically accumulated personal health information of a user such that the personal health information can be used as critical information by which a disease cause and the like can be fundamentally understood during an incidence of a disease in the future.

INDUSTRIAL APPLICABILITY

The present invention enables to easily and periodically acquire, without regard to place and time, personal health information and cause the acquired personal health information to be continuously accumulated and managed over a long time by analyzing, storing, and making the same into data, by which a disease cause can be fundamentally understood during an incidence of a disease in the future.

The invention claimed is:

1. A device for acquiring personal health information that includes, as an image information acquiring unit for acquiring image information on any one of a skin image used to diagnose skin; an ear, a nose, and a mouth image used to diagnose an ear, a nose, and a throat; and a teeth image used to diagnose teeth, an LED light for emitting light to a subject to cause the light to be projected thereon, an LED driver for driving the LED light, a general purpose input/output (GPIO) expander for controlling the LED driver to turn on the LED light, a lens for passing image information projected and reflected by the LED light, and a CAM sensor (C-MOS sensor) for receiving the image information that has passed through the lens and converting the image information into a YUV video signal to be transmitted to a USB back end 5, the device comprising:

a moisture sensor for acquiring moisture of skin with a built-in microcomputer to cause the acquired information to be transmitted to the USB back end via I2C communication, a human body temperature sensor for acquiring body temperature of a human body with a built-in microcomputer to cause the acquired information to be transmitted to the USB back end via I2C communication, a temperature/humidity sensor for acquiring an ambient temperature and humidity of a person who undergoes an examination with a built-in microcomputer (not shown) to cause the acquired information to be transmitted to the USB back end via I2C communication, the USB back end for causing the image information received as the YUV signal from the CAM sensor in the image information acquiring unit and the health care information received from the moisture sensor, the human body temperature sensor, and the temperature/humidity sensor via I2C communication to be converted into a USB standard signal, in which the image information and the health care information transmitted to the USB back end are transmitted as a USB standard signal to a personal terminal or a personal computer (PC) via a USB port, and an electrically erasable programmable read-only memory EEPROM for communicating with the USB back end via I2C communication to allow the USB back end to make a correct and smooth interface between the CAM sensor (C-MOS sensor), the moisture sensor, the human body temperature sensor, and the temperature/humidity sensor, and the personal terminal and the personal computer for the image information and the health care information.

2. A device for acquiring personal health information that includes, as an image information acquiring unit for acquiring image information on any one of a skin image used to diagnose skin; an ear, a nose, and a mouth image used to diagnose an ear, a nose, and a throat; and a teeth image used to diagnose teeth, an LED light for emitting light to a subject to cause the light to be projected thereon, an LED driver for driving the LED light, a general purpose input/output (GPIO) expander for controlling the LED driver to turn on the LED light, a lens for passing image information projected and reflected by the LED light, and a CAM sensor (C-MOS sensor) for receiving the image information that has passed through the lens and converting the image information into a YUV video signal to be transmitted to a USB back end 5, the device comprising:

a moisture sensor for acquiring moisture of skin with a built-in microcomputer to cause the acquired information to be transmitted to the USB back end via I2C communication, the USB back end for causing the image information received as the YUV signal from the CAM sensor in the image information acquiring unit and the health care information received from the moisture sensor via I2C communication to be converted into a USB standard signal, in which the image information and the health care information transmitted to the USB back end are transmitted as USB standard signal to a personal terminal or a personal computer (PC) via a USB port, and an electrically erasable programmable read-only memory EEPROM for communicating with the USB back end via I2C communication to allow the USB back end to make a correct and smooth interface between the CAM sensor (C-MOS sensor) and the moisture sensor, and the personal terminal and the personal computer for the image information and the health care information.

3. A device for acquiring personal health information that includes, as an image information acquiring unit for acquiring image information on any one of a skin image used to diagnose skin; an ear, a nose, and a mouth image used to diagnose an ear, a nose, and a throat; and a teeth image used to diagnose teeth, an LED light for emitting light to a subject to cause the light to be projected thereon, an LED driver for driving the LED light, a general purpose input/output (GPIO) expander for controlling the LED driver to turn on the LED light, a lens for passing image information projected and reflected by the LED light, and a CAM sensor (C-MOS sensor) for receiving the image information that has passed through the lens and converting the image information into a YUV video signal to be transmitted to a USB back end 5, the device comprising:

a human body temperature sensor for acquiring body temperature of a human body with a built-in microcomputer to cause the acquired information to be transmitted to the USB back end via I2C communication, the USB back end for causing the image information received as the YUV signal from the CAM sensor in the image information acquiring unit and the health care information received from the human body temperature sensor via I2C communication to be converted into a USB standard signal, in which the image information and the health care information transmitted to the USB back end are transmitted as USB standard signal to a personal terminal or a personal computer (PC) via a USB port, and an electrically erasable programmable read-only memory EEPROM for communicating with the USB back end via I2C communication to allow the USB back end to make a correct and smooth interface between the CAM sensor (C-MOS sensor) and the human body temperature sensor, and the personal terminal and the personal computer for the image information and the health care information.

* * * * *